United States Patent
Chutka et al.

(10) Patent No.: US 10,973,856 B2
(45) Date of Patent: Apr. 13, 2021

(54) ECM IMPLANT COMPOSITIONS AND METHODS

(71) Applicant: Cook Biotech Incorporated, West Lafayette, IN (US)

(72) Inventors: Michelle Chutka, West Lafayette, IN (US); Michael C. Hiles, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 14/211,234

(22) Filed: Mar. 14, 2014

(65) Prior Publication Data

US 2014/0275290 A1  Sep. 18, 2014

Related U.S. Application Data

(60) Provisional application No. 61/802,113, filed on Mar. 15, 2013.

(51) Int. Cl.
| | |
|---|---|
| *A61K 35/38* | (2015.01) |
| *A61K 35/22* | (2015.01) |
| *C08J 3/00* | (2006.01) |
| *A61L 27/36* | (2006.01) |
| *A61L 27/56* | (2006.01) |

(52) U.S. Cl.
CPC .............. *A61K 35/38* (2013.01); *A61K 35/22* (2013.01); *A61L 27/3633* (2013.01); *A61L 27/56* (2013.01); *C08J 3/00* (2013.01)

(58) Field of Classification Search
None
See application file for complete search history.

(56) References Cited

U.S. PATENT DOCUMENTS

| | | | |
|---|---|---|---|
| 7,959,941 B2 | 6/2011 | Knaack et al. | |
| 2003/0143258 A1* | 7/2003 | Knaack et al. | ............... 424/426 |
| 2006/0246033 A1* | 11/2006 | Ninan | ................... A61K 35/38 |
| | | | 424/85.5 |
| 2006/0292227 A1* | 12/2006 | McPherson | ............ A61K 35/38 |
| | | | 424/551 |
| 2009/0092651 A1 | 4/2009 | Shah et al. | |
| 2009/0246244 A1* | 10/2009 | McKay et al. | ................ 424/423 |
| 2009/0326577 A1* | 12/2009 | Johnson | ............. A61B 17/0057 |
| | | | 606/213 |
| 2010/0266654 A1 | 10/2010 | Hodde et al. | |
| 2011/0150998 A1 | 6/2011 | Farrell et al. | |

FOREIGN PATENT DOCUMENTS

| | | |
|---|---|---|
| JP | 2008-509924 A | 4/2008 |
| JP | 2011-525140 A | 9/2011 |
| WO | WO 2004/053112 | 6/2004 |
| WO | WO 2006/020773 A3 | 2/2006 |
| WO | WO 2009/155607 | 12/2009 |

OTHER PUBLICATIONS

English Abstract of US2009317469 corresponding to JP 2011-525140 obtained from Espacenet on Aug. 29, 2019.
English Abstract of WO2006020773 corresponding to JP 2008-509924 obtained from Espacenet on Aug. 29, 2019.

* cited by examiner

*Primary Examiner* — Emily A Cordas
(74) *Attorney, Agent, or Firm* — Woodard Emhardt Henry Reeves & Wagner LLP

(57) ABSTRACT

Described our medical compositions and methods including a particulate extracellular matrix tissue in admixture with sugar. Such medical compositions, in dried forms, can demonstrate enhanced rehydration properties. Medical compositions and products as described herein find particular use in treating diseased and/or damaged tissue, such as wound repair. Related methods of manufacture and use are also described.

23 Claims, 3 Drawing Sheets

ECM IMPLANT COMPOSITIONS AND METHODS

REFERENCE TO RELATED APPLICATIONS

The present application claims the benefit of U.S. Provisional Patent Application Ser. No. 61/802,113 filed Mar. 15, 2013 entitled ECM IMPLANT COMPOSITIONS AND METHODS which is hereby incorporated by reference in its entirety.

BACKGROUND

The present invention resides generally in the field of medical compositions and in particular aspects to medical compositions that incorporate extracellular matrix materials.

As further background, a variety of extracellular matrix (ECM) materials have been proposed for use in medical grafting, cell culture, and other related applications. For instance, medical grafts and cell culture materials containing submucosa derived from small intestine, stomach, or urinary bladder tissues, have been proposed. See, e.g. U.S. Pat. Nos. 4,902,508, 4,956,178, 5,281,422, 5,554,389, 6,099,567 and 6,206,931. Medical materials derived from liver basement membrane have also been proposed, for example in U.S. Pat. No. 6,379,710. As well, ECM materials derived from amnion (see e.g. U.S. Pat. Nos. 4,361,552 and 6,576,618) and from renal capsule membrane (see International PCT Patent Application No. WO/03/002165 published Jan. 9, 2003) have been proposed for medical and/or cell culture applications. In addition, Cook Biotech Incorporated, West Lafayette, Ind., currently manufactures a variety of medical products based upon small intestinal submucosa under the trademarks SURGISIS®, STRATASIS® and OASIS®.

In certain applications, medical materials have been formed into fluidized compositions and used in conjunction with a variety of components directed towards treating a particular condition. For example, U.S. Pat. No. 6,206,931 describes forming a fluidized composition from an extracellular matrix material. Such fluidized compositions are typically formed into gels for use as an injectable graft. Similarly, International PCT Application No. WO 05/020847 discloses an ECM material formed as a gel and including a bioactive component, such as FGF-2. This gel material can also include a particulate ECM material, which is suggested to provide additional material that can function to provide bioactivity to the gel and/or serve as scaffolding material for tissue ingrowth.

A need remains for additional medical compositions and products that can be used in a wide variety of medical applications. The present invention provides such medical compositions and products, as well as methods for preparing and using the same.

SUMMARY

In certain aspects, the present disclosure pertains to formable medical compositions that include a particulate ECM tissue material. The formable composition may for example be a shape retaining but formable putty material.

Some embodiments herein provide a medical composition including a particulate of a collagenous extracellular matrix (ECM) material, where the composition has enhanced rehydration properties. In accordance with some forms of the disclosure, such medical compositions comprise a particulate ECM tissue and a sugar, preferably fructose. The compositions are in dry form, but are wettable with an aqueous medium, and the compositions may be in the form of a dried porous body. Such wetting, with an appropriate amount of the aqueous medium, can form a shape retaining but formable putty material. Such a putty material can include particles of the particulate ECM tissue bound in slidable relation with one another by an aqueous solution of the fructose and/or other sugar Other embodiments of the present disclosure provide methods for preparing a material for treatment of diseased or damaged tissue. In one form, the methods comprise drying an admixture of materials including a particulate of comminuted extracellular matrix material, a sugar such as fructose, and a liquid, preferably to form a porous body. The drying step may comprise lyophilization of the admixture.

In other embodiments, the disclosure provides methods of preparing a material for treating diseased or damaged tissue. The methods comprise rehydrating a dried body comprising a particulate ECM tissue and a sugar, preferably fructose. In one form, the rehydrating comprises contacting the dried body with an aqueous medium. The aqueous medium may in some embodiments comprise blood or a blood fraction, including for example serum or platelet-rich plasma. In certain embodiments, the blood or blood fraction may be autologous or allogenic to an intended recipient subject, such as a human subject, for the material. In accordance with certain inventive variants, the method further includes applying the material to diseased or damaged tissue of a recipient subject.

In still further embodiments, the disclosure provides a putty comprising a particulate ECM tissue, a sugar (preferably fructose), and an aqueous medium. The putty is desirably shape retaining but formable. The putty can include particles of the particulate ECM tissue bound in slidable relation with one another by an aqueous solution of the fructose and/or other sugar. The aqueous medium can in some embodiments include blood or a blood fraction, including for example serum or platelet-rich plasma. The blood or blood fraction, when used, may be autologous or allogenic to an intended recipient subject, such as a human subject, for the material.

In accordance with any of the method or product compositions disclosed herein, one or more of the following additional features may be included:

(a) the particulate ECM tissue can include at least one growth factor retained from a source tissue for the particulate ECM tissue;

(b) the method or product is for treatment of diseased and/or damaged tissue, for example a wound or a cutaneous ulcer;

(c) the particulate ECM tissue comprises submucosa, such as intestinal, urinary bladder, stomach, or small intestinal submucosa (SIS);

(d) the method or product can incorporate fructose as the only sugar in the composition, or fructose can be used in combination with one or more other sugars;

(e) the particulate ECM tissue and sugar may be included in any ratio with respect to one another disclosed herein;

(f) a putty material can have any of the ratios or compositional levels of particulate ECM tissue, sugar, and/or aqueous medium disclosed herein.

Additional embodiments, as well as features and advantages of embodiments of the invention, will be apparent from the description herein.

DESCRIPTION OF THE SELECTED EMBODIMENTS

Figure 1:
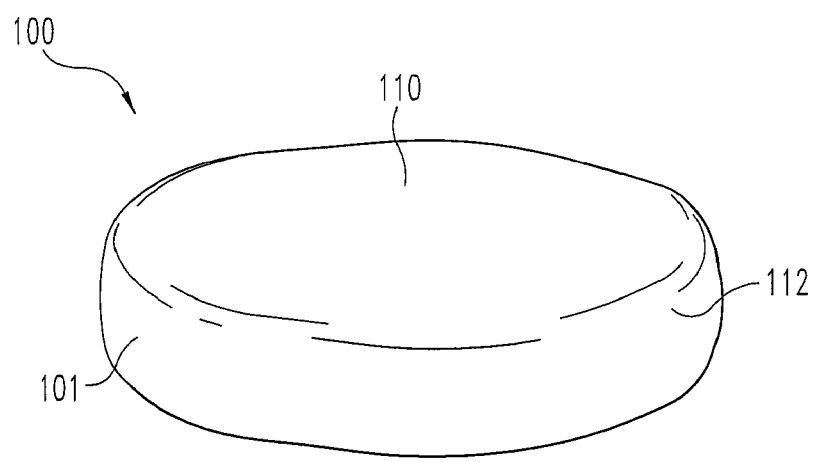
FIG. 1 is a perspective view of one embodiment of a dried body of the present disclosure.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated device, and further applications of the principles of the disclosure as illustrated therein are herein contemplated as would normally occur to one skilled in the art to which the disclosure relates.

As disclosed above, aspects of the present disclosure relate to novel methods and materials for treating diseased or damaged tissue in a patient. In certain aspects, the disclosure relates to materials comprising a particulate ECM tissue and a sugar, preferably fructose. As will be discussed herein, it has been found that addition of substantial amounts of sugar to a composition including the particulate ECM material results in accelerated rehydration times and increased aqueous medium uptake by the particulate.

The ECM tissue used to prepare the particulate ECM is typically a collagenous material. For example, suitable collagenous ECM materials include those comprising submucosa, renal capsule membrane, dermal collagen, dura mater, pericardium, fascia lata, serosa, peritoneum or basement membrane layers, including liver basement membrane. These or other ECM materials that occur as connective tissue sheets in soft tissue of the patient, and that can be isolated as such sheets, are preferred. Suitable submucosa-containing ECM materials for these purposes include, for instance, ECMs including intestinal submucosa (e.g. small intestinal submucosa), stomach submucosa, urinary bladder submucosa, and uterine submucosa. Collagenous ECM materials comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

In some aspects, a typical layer thickness for an isolated submucosa or other ECM connective tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue layers utilized desirably retain a structural microarchitecture from the source tissue, including structural fiber proteins such as collagen and/or elastin that are non-randomly oriented. Such non-random collagen and/or other structural protein fibers can in certain embodiments provide an ECM tissue that is non-isotropic in regard to tensile strength, thus having a tensile strength in one direction that differs from the tensile strength in at least one other direction. When processed to a particulate ECM tissue, at least some of this structural microarchitecture can remain in the individual particles.

The particulate ECM tissue is advantageously a remodelable material that promotes the formation of new tissue in the patient as the implanted or applied ECM tissue is resorbed. The particulate ECM material can exhibit angiogenic properties and promote cellular invasion and ingrowth.

The particulate ECM tissue material may include one or more bioactive factors. Suitable bioactive agents may include one or more bioactive factors native to the source tissue for the ECM tissue. For example, a submucosa or other ECM tissue material may retain one or more native growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials may retain other native bio active factors such as but not limited to proteins, glycoproteins, proteoglycans, and glycosaminoglycans. For example, ECM materials may include native heparin, heparin sulfate, hyaluronic acid, fibronectin, cytokines, and the like. Thus, generally speaking, a particulate submucosal or other particulate ECM tissue material may retain one or more bioactive components that induce, directly or indirectly, a cellular response such as a change in cell morphology, proliferation, growth, and protein or gene expression.

Particulate ECM materials used in the invention will typically include abundant collagen, most commonly being constituted at least about 80% by weight collagen on a dry weight basis. Naturally-derived ECM materials typically include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

The particulate ECM material will typically be porous. The porosity of the ECM material can be controlled to some extent by processing techniques. For example the porosity of the ECM material can be reduced by drying the material under compression, for example by drying a starting material ECM layer prior to comminution, or the formed particulate, under compression. On the other hand, an relatively higher porosity ECM material can be prepared by drying the ECM material by lyophilization, for example by freeze drying or evaporative cooling techniques. Such porosity-reducing or porosity-maintaining or porosity-increasing techniques can be used to provide the particulate ECM material with a desired level of porosity for a particular application.

The submucosa-containing or other ECM material used in the present invention may also exhibit an angiogenic character and thus be effective to induce angiogenesis in a host treated with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and others. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure, or during or after application of the material to the patient.

The particulate ECM material used in aspects herein can be xenogenic, allogenic, or autologous relative to the treated patient. As well, additional materials incorporated in the compositions herein may also be animal-derived, and may be xenogenic, allogenic, or autologous relative to the treated patient. In certain aspects, a human patient will be treated with a composition comprising a xenogenic particulate ECM tissue (e.g. porcine-, bovine- or ovine-derived) that is combined in the composition with a human material(s) that is/are autologous or allogenic relative to the human patient.

With respect to the particulate, it particulate can be formed by cutting, tearing, grinding or otherwise, comminuting a larger, decellularized ECM connective tissue layer material as described above to form a particulate. For example, cryogrinding or milling operations can be used to form the particulate ECM tissue material from larger layer. These comminution processes can form random fragments of the ECM tissue layer. The particle size of the particulate ECM tissue can vary. In preferred aspects, the average particle size of the particulate ECM tissue will be in the range of about 20 microns to about 500 microns, more preferably about 50 microns to about 400 microns. The particulate ECM tissue incorporated into compositions of this disclosure can be an unfractionated particle population prepared by the comminution, or can be a fractions of the particle population prepared by the comminution. Such fractions can for example be obtained by conventional techniques such as screening or sieving.

As disclosed above, compositions of the invention also include a (at least one) sugar. The sugar may, for example, be a simple sugar such as fructose or glucose, or another sugar such as sucrose. These or other monosaccharide or disaccharide sugars are preferred, and fructose is particularly preferred. Such sugars are generally available commercially (including United States Pharmacopeia (USP) grade) as powders, and can be used in that form herein, at least as starting materials or as materials incorporated into dry compositions herein. Fructose is preferred for inclusion in or as the sugar component of the dried compositions or putties herein, and can constitute at least 50% of the sugar, at least 75% of the sugar, at least 90% of the sugar, at least 99% of the sugar, or all or essentially all of the sugar included in the dried composition or putty composition.

The incorporation of a sugar such as fructose in dried compositions disclosed herein can not only improve rehydration rate but can also increase the aqueous medium (e.g. serum, blood, saline, water) uptake of the compositions. Additionally or alternatively, the incorporation of the fructose and/or other sugar can also improve the physical characteristics of the dried composition and of a putty prepared from the dried composition. For example, dried bodies including the sugar and the particulate ECM tissue can be less friable and less prone to contact-initiated surface disintegration than corresponding dried bodies including only the particulate ECM tissue. As well, superior shape retaining but formable putties can result from hydration of a material including the sugar and the particulate ECM tissue than from hydration of a corresponding material including only the particulate ECM tissue.

To prepare dried compositions herein, the sugar, particulate ECM material, and any other components to be included in the dried composition, can be admixed in any suitable fashion. Illustratively, the materials can be formed into an admixture by dry mixing the particulate ECM material with the sugar and potentially other dry ingredients, or by combining a solution or suspension of one or more of the components with another solution or dry material. Where a dried body composition is to be prepared, the admixed materials, while hydrated with water or another suitable liquid, can be subjected to drying conditions, preferably lyophilization, to form the dried body. This drying can be conducted with the hydrated admixture in a mold or form to result in a regularly shaped dried body that takes on contours imparted by the mold or form. The dried body is desirably porous. According to certain non limiting embodiments, the composite dried body may be spherical, tablet shaped, oblong, or cylindrical. In preferred embodiments, the dried body is shaped as a disc. In some forms, a dried body herein will weigh about 0.5 g to 5 g. In certain preferred forms, the dried body weighs about 1 g to about 3 g. Such dried bodies can be formulated to form a shape retaining but formable putty upon hydration with a liquid such as described herein. In some forms the dried body is sterilized. The dried body can thus be sterilely enclosed in a medical package to provide a medical product.

A variety of aqueous media or other materials including biocompatible liquids can be used in the preparation of putty compositions herein. Examples of suitable aqueous mediums include but are not limited to: water, saline, blood or blood fractions, blood serum, platelet rich plasma, serum albumin, bone marrow, bone marrow fractions, cell-containing (including stem-cell containing) preparations isolated from the patient or another subject, and phosphate buffered saline (PBS). Combinations of these mediums with each other or with other suitable liquid mediums may also be used. It will be understood that aqueous or other mediums that can be combined with dried materials herein may include non-liquid components, but will nonetheless include liquid component(s) that will provide the liquid content of the prepared putty compositions as specified herein.

Putty compositions of the invention can include appropriate ratios of particulate ECM tissue, sugar, and liquid to one another, and appropriate overall levels of these components in the putty composition, in order to provide the desired physical properties to the putty. The preferred putty composition is shape retaining, but formable to a new shape by application of force. Still further, the preferred putty can exhibit cohesiveness such that upon deformation the putty does not form cracks but instead flows to a new shape while retaining an intact continuous material matrix. For solid components such as the ECM particulate and sugar, unless indicated otherwise, the ratios and percentages expressed herein are expressed on a dry weight basis.

In certain aspects, the weight ratio of liquid to total solids in the putty is about 3:1 to about 7:1, or about 4:1. Additionally or alternatively, the weight ratio of liquid to particulate ECM tissue in the putty is about 5:1 to about 10:1, or about 6:1. Additionally or alternatively, the weight ratio of particulate ECM tissue to sugar (expressed as total sugars when more than one is included) in the putty can be about 10:1 to about 1:1, about 5:1 to about 1:1, about 3:1 to about 1:1, or about 2:1 (these particulate ECM tissue:sugar weight ratios also apply to dried compositions, e.g. dried bodies, herein).

In respect of overall composition levels of these components, the putty can be constituted about 70% to about 90% by weight of liquid, or about 75% to about 85% of liquid, or about 80% of liquid. Additionally or alternatively, the putty can be constituted about 5% to about 20% by weight of the particulate ECM tissue, or about 10% to about 15% of the particulate ECM tissue, or about 13% of the particulate ECM tissue. Additionally or alternatively, the putty can be constituted about 2% to about 10% by weight of the sugar, or about 5% to about 8%, or about 6% to about 8%.

It will be understood that the putty may include materials other than the liquid, the particulate ECM tissue, and the sugar. In preferred forms, however, the liquid, the particulate ECM tissue, and the sugar, will constitute at least about 70% by weight of the putty, at least about 80% of the putty, at least about 90% of the putty, at least about 95% of the putty, at least about 99% of the putty, or all or essentially all of the weight of the putty, in various embodiments. Additionally or alternatively, for dried bodies or other dried compositions herein, in preferred embodiments, the particulate ECM and the sugar will at least about 70% by weight of the dried composition, at least about 80% of the dried composition, at least about 90% of the dried composition, at least about 95% of the dried composition, at least about 99% of the dried composition, or all or essentially all of the weight of the dried composition, in various embodiments.

Other materials that may be included in the dried compositions and/or the putty composition include, as examples, bioactive components as identified in discussions above, sclerosants such as sodium tetradecyl sulfate, additional scaffolding and/or bioactive materials including for example bone particles, demineralized bone matrix particles, calcium phosphate particles, ceramic particles, cells (including but not limited to stem cells), osteogenic particles or other substances, and others. These materials may be included in the putty in any suitable fashion, for example either as materials within dried compositions to be rehydrated, or as materials dissolved or suspended in rehydrating mediums, or as materials added separately to a formed putty.

In some forms, the present disclosure relates to compositions as discussed above that have been sterilized or methods which include sterilizing such a composition. Sterilization may be conducted in any suitable manner, including for example ethylene oxide sterilization and/or irradiative sterilization, e.g. gamma ray or electron beam sterilization.

The discussions below refer to embodiments depicted in the Figures. It will be understood that these specific disclosed embodiments can include any of the compositional or technique features disclosed hereinabove, and similarly that the compositions and methods disclosed above can include any feature depicted in the Figures or specifically described in conjunction with the Figures.

Turning now to FIG. 1, illustrated is a dried body 100 in accordance with some forms of the disclosed, dried composition. In some forms the dried body 100 comprises a porous composite material 101 comprising an admixture of a particulate ECM mixed with fructose and/or another sugar. In some forms, the dried body 100 is substantially flat, having at least a planar surface 110, and an edge surface 112.

Figure 2:
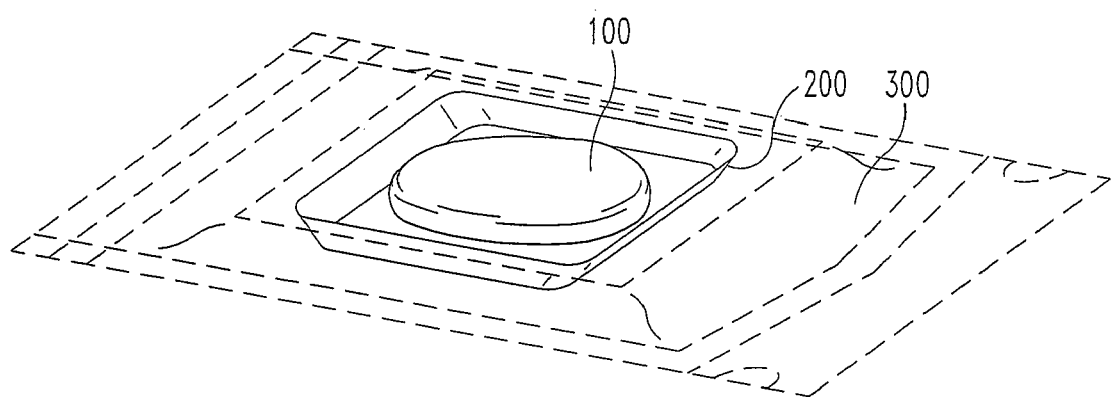
FIG. 2 is a perspective view of one embodiment of a dried body of the present disclosure including one form of packing the device.

In accordance with certain inventive variants, the dried body 100 of the present disclosure may be packaged in a sterilized container, as shown in FIG. 2. In some forms the container 200 is a tray, or saucer. In certain forms, the container comprises polystyrene or any other suitable material compatible with sterilization. In some forms, the tray may be sealed within a sterilizable medical packaging pouch 300. It will be understood for aspects herein that medical packaging other than that specifically shown in FIG. 2, that also sterilely encloses the dried body 100 or any other inventive composition described herein, may be used.

In some forms, the disclosure also relates to a method of preparing a material for treating diseased and/or damaged tissue. In certain embodiments, the method comprises obtaining a dried body comprising extracellular matrix particulate and fructose. In some forms, the dried body is substantially as described above. In accordance with certain modes of practicing the disclosed method, the dried body is rehydrated, for example with an aqueous medium as described herein, to form a paste. The composition formed by the rehydration of the dried body may be of any suitable consistency for treated the targeted tissue.

In further embodiments, a putty composition as described herein is applied to a patient, such as a human or veterinary patient, for instance to treat diseased and/or damaged tissue. The composition may be applied by any suitable technique including, for example, injecting, spreading, infusing, filling, compressing, packing and/or engrafting. A diseased or damaged tissue to be treated may be any of a variety of such tissues, including soft and hard tissues such as skin, muscle, body wall tissue, connective tissue, ligaments, tendons, bone, and others. Illustratively, in some forms the putty can be forced into contact with tissue surfaces so as to conform to those tissues and promote repair, which repair may include the development of new tissue of the patient. In certain preferred treatments, the putty is applied to an open cutaneous wound of a patient, for example a cutaneous ulcer such as a diabetic ulcer, a burn, or other partial or full-thickness cutaneous wound.

To promote a further understanding of embodiments disclosed herein and their features and advantages, the following specific Examples are provided. It will be understood that these examples are illustrative, and not limiting, in nature.

Example 1

Rehydration Time of Extracellular Matrix Particulate

Frozen particulate extracellular matrix tissue (comminuted small intestine submucosa) was provided as a starting material. The frozen particulate was divided into 10 g portions and thawed. 50 mg, 100 mg, 200 mg, or 500 mg D-Fructose USP was added to each 10 g portion of hydrated particulate ECM tissue (which equaled about 1 g dry weight of particulate ECM tissue). The combined materials were mixed in back and forth via two luer-locked syringes and dispensed into a 3.5"×3.5"×1" polystyrene weigh boat. The mixture was then lyophilized in the weigh boat to create a flat, dried, porous body.

Figure 3:
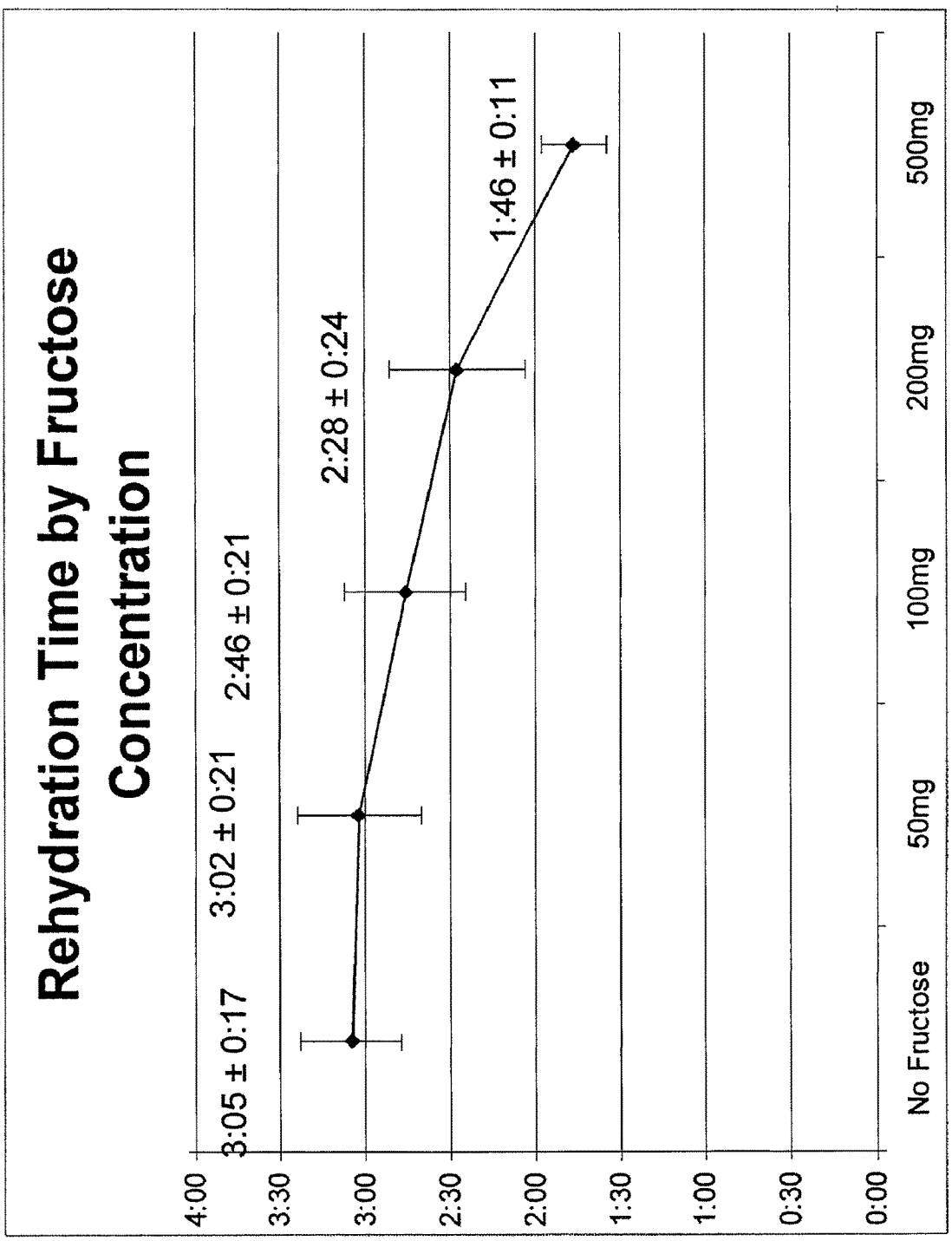
FIG. 3 is a graphical representation of rehydration time date per fructose concentration.

The dried bodies were rehydrated using 6 mL of 4% BSA in 1× phosphate buffered saline. A metal spatula was used as needed to manipulate the sample and submerse in fluid. A timer was used to measure the time elapsed between addition of the fluid to when the sample was fully rehydrated as evidenced by the capacity to form a cohesive, shape-retaining ball. The results of the rehydration assay are reported in FIG. 3. Illustratively, the samples containing 500 mg of fructose exhibited an average rehydration time of 1:46, control samples without fructose exhibited an average rehydration time of 3:05.

Example 2

Serum Uptake of Extracellular Matrix Particulate

Figure 4:
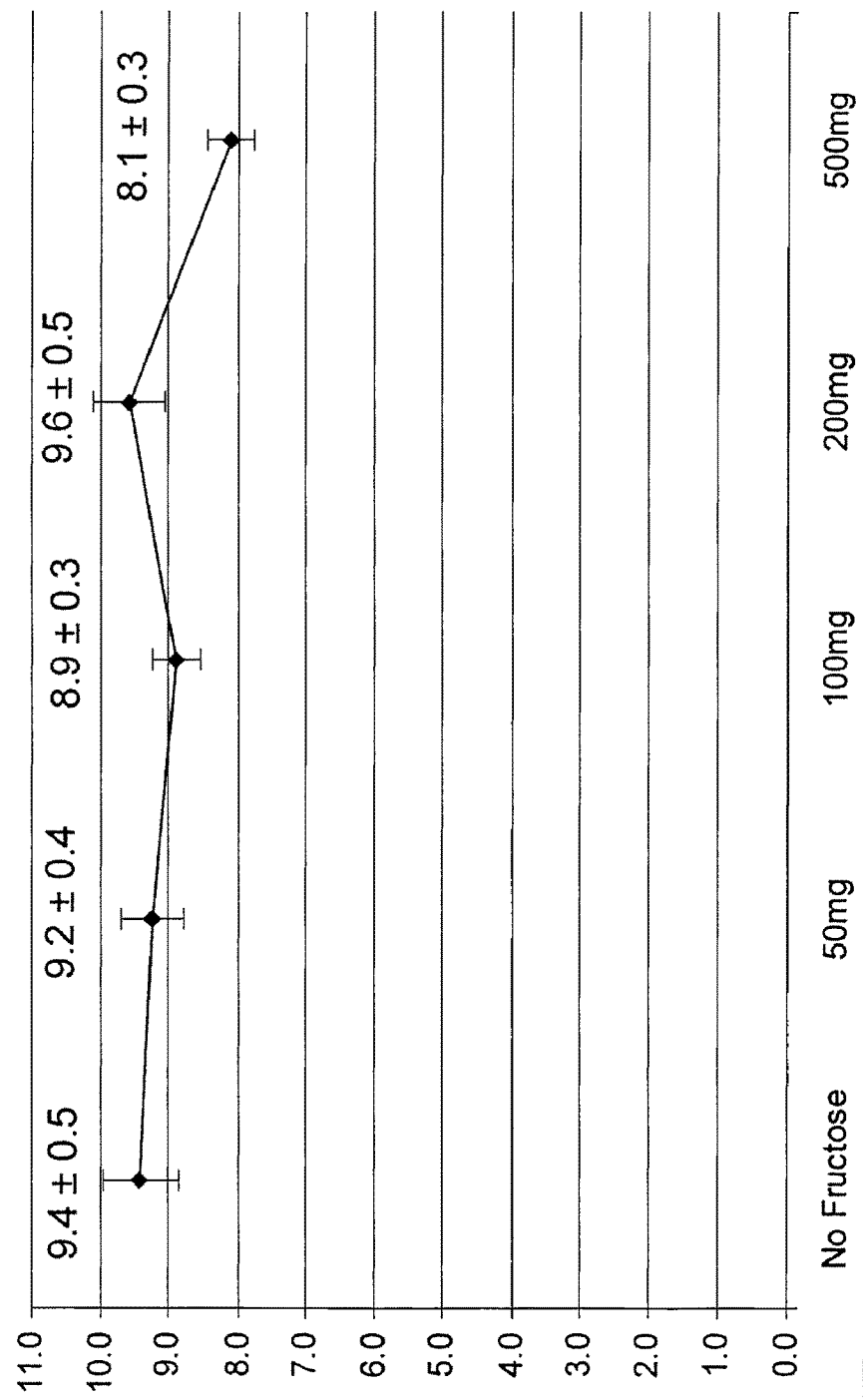
FIG. 4 is a graphical representation of serum uptake data per fructose concentration.

Dried bodies prepared as in Example 1 were first rehydrated using 6 mL of 4% BSA in 1×PBS as described in Example 1. To the rehydrated bodies was added additional fluid in 1 mL increments until the sample could no longer retain a cohesive shape. The total amount of fluid each sample could uptake before losing its cohesive shape was recorded. The results of the serum uptake assay are reported in FIG. 4. Illustratively, the samples containing 200 mg of fructose were able to remain cohesive while absorbing an average of 9.6 mL of fluid, control samples without fructose absorbed an average of 9.4 mL of fluid.

The use of the terms "a" and "an" and "the" and similar referents in the context of describing the invention especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical composition comprising:
an admixture comprising a particulate extracellular matrix (ECM) tissue and fructose wherein said particulate extracellular matrix tissue comprises comminuted extracellular matrix material, wherein the weight ratio of particulate ECM tissue to said fructose is about 3:1 to about 1:1, and wherein said comminuted extracellular matrix material includes native bioactive factors retained from a source tissue for the comminuted extracellular matrix material, the native bioactive factors comprising native non-collagenous solids, and wherein the native non-collagenous solids constitute at least 1% of the total dry weight of the particulate extracellular matrix material, and wherein the native bioactive factors comprise native growth factors, proteins, glycoproteins, proteoglycans, and glycosaminoglycans, wherein:
said admixture is in the form of a dried porous body wettable with an aqueous medium to form a shape retaining but formable putty, and wherein said particulate extracellular matrix tissue and said fructose comprise at least 70% by weight of said dried composition; or said admixture is in the form of a shape-retaining but formable putty also comprising an aqueous medium, and wherein said particulate extracellular matrix tissue, said fructose, and said aqueous medium comprise at least 70% by weight of said putty.

2. The medical composition of claim 1, wherein:
said admixture is present in a dried, porous body, and wherein said dried porous body has a mass of about 0.5 g to about 5 g.

3. The medical composition of claim 1, wherein said aqueous medium comprises a blood fraction.

4. The medical composition of claim 1, wherein said aqueous medium comprises cells.

5. The medical composition of claim 1, wherein said admixture is in the form of a dried porous body, and wherein said particulate extracellular matrix tissue and said fructose comprise at least 70% by weight of said dried composition.

6. The medical composition of claim 1, wherein said admixture and said aqueous medium is in the form of a putty, and wherein said particulate extracellular matrix tissue, said fructose, and said aqueous medium comprise at least 70% by weight of said putty.

7. The medical composition of claim 1, wherein said growth factors comprise basic fibroblast growth factor, transforming growth factor beta, epidermal growth factor, cartilage derived growth factor, and/or platelet derived growth factor.

8. The medical composition of claim 5, wherein said particulate extracellular matrix tissue and said fructose comprise at least 90% by weight of said dried composition.

9. The medical composition of claim 8, wherein said particulate extracellular matrix tissue and said fructose comprise at least 95% by weight of said dried composition.

10. The medical composition of claim 6, wherein said particulate extracellular matrix tissue, said fructose, and said aqueous medium comprise at least 90% by weight of said putty.

11. The medical composition of claim 10, wherein said particulate extracellular matrix tissue, said fructose, and said aqueous medium comprise at least 95% by weight of said putty.

12. A medical product comprising:
a dried porous body comprising an admixture of a particulate extracellular matrix tissue and fructose, wherein the weight ratio of particulate extracellular matrix tissue to said fructose is about 3:1 to 1:1, said particulate extracellular matrix tissue including native bioactive factors retained from a source tissue for the particulate extracellular matrix tissue, the native bioactive factors comprising native non-collagenous solids and constituting at least 1% of the total dry weight of the particulate extracellular matrix tissue, wherein the native bioactive factors comprise native growth factors, proteins, glycoproteins, proteoglycans, and/or glycosaminoglycans, and wherein said particulate extracellular matrix tissue and said fructose comprise at least 90% by weight of said dried porous body.

13. The medical composition of claim 12, wherein said particulate extracellular matrix tissue and said fructose comprise at least 95% by weight of said dried porous body.

14. The medical composition of claim 12, further comprising a tray and wherein said dried porous body is sterilely packaged on said tray.

15. A medical product comprising:
a dried porous body comprising an admixture of a particulate extracellular matrix tissue and a sugar component comprising fructose, wherein the weight ratio of particulate extracellular matrix tissue to said fructose is about 3:1 to 1:1, said particulate extracellular matrix tissue including native bioactive factors retained from a source tissue for the particulate extracellular matrix tissue, the native bioactive factors comprising native non-collagenous solids and constituting at least 3% of the total dry weight of the particulate extracellular matrix tissue, wherein the native bioactive factors comprise native growth factors, proteins, glycoproteins, proteoglycans, and glycosaminoglycans, wherein said native growth factors comprise: basic fibroblast growth factor, transforming growth factor beta, and platelet derived growth factor, and wherein said particulate extracellular matrix tissue and said sugar component comprise at least 90% by weight of said dried porous body.

16. A method of preparing a medical composition as described in claim 1, the method comprising:
drying an admixture of materials including a particulate extracellular matrix tissue, fructose, and a liquid, so as to form said dried porous body of claim 1.

17. The method of claim 16, wherein:
said drying comprises lyophilizing.

18. The method of claim 16 further comprising locating the admixture in a mold, and wherein said drying is conducted with the admixture in the mold.

19. The method of claim 16, wherein:
said particulate extracellular matrix tissue comprises submucosa.

20. A method of preparing a material for treating a patient, comprising:
wetting said dried porous body of claim 1 with an aqueous medium to form a shape retaining but formable putty.

21. The method of claim 20, wherein:
said rehydrating is conducted sufficiently to form a shape-retaining but formable putty.

22. The method of claim 20, wherein:
said rehydrating includes combining an aqueous medium with the dried body.

23. The method of claim 22, wherein:
said aqueous medium is or includes blood, blood serum or a blood fraction, and wherein said blood, blood serum or blood fraction is autologous to a subject that is to be treated with the material.

* * * * *